US006185451B1

(12) United States Patent
Richardson et al.

(10) Patent No.: US 6,185,451 B1
(45) Date of Patent: Feb. 6, 2001

(54) MUSCLE FUNCTION ASSESSMENT APPARATUS AND METHOD

(75) Inventors: Carolyn Anne Richardson, St. Lucia; Gwendolen Anne Jull, The Gap; Paul Hodges, Randwick; Julie Hides, Chapel Hill, all of (AU)

(73) Assignee: The University of Queensland, St. Lucia (AU)

( * ) Notice: Under 35 U.S.C. 154(b), the term of this patent shall be extended for 0 days.

(21) Appl. No.: 09/435,946

(22) Filed: Nov. 9, 1999

Related U.S. Application Data

(63) Continuation of application No. PCT/AU98/00340, filed on May 8, 1998.

(30) Foreign Application Priority Data

May 9, 1997 (AU) .................................................. P06739

(51) Int. Cl.[7] .................................................. A01B 5/04
(52) U.S. Cl. .................................... 600/546; 600/587
(58) Field of Search ................................ 600/546, 587, 600/595

(56) References Cited

U.S. PATENT DOCUMENTS

| 4,655,227 | 4/1987 | Gracovetsky . | |
|---|---|---|---|
| 5,357,973 | * 10/1994 | Sunouchi et al. | 600/546 |
| 5,662,118 | * 9/1997 | Skubick | 600/546 |
| 5,755,675 | * 5/1998 | Sihvonen | 600/591 |
| 5,916,172 | * 6/1999 | Hodges et al. | 600/546 |

FOREIGN PATENT DOCUMENTS

WO 94/07414    4/1994  (WO) .

OTHER PUBLICATIONS

Miller, Marilyn, et al.: "Recruitment of Internal Oblique and Transversus Abdominis Muscles During the EccentricPhase of the Curl–up Exercise", *Physical Therapy*, vol. 67(8), Aug. 1987, pp. 1213–1217.

* cited by examiner

*Primary Examiner*—Cary O'Connor
*Assistant Examiner*—Pamela Wingood
(74) *Attorney, Agent, or Firm*—Townsend & Townsend & Crew LLP

(57) ABSTRACT

A method and apparatus for assessing the function of deep joint stabilizing muscles. Superficial muscles are monitored using an EMG (3) during performance of an activity known to require recruitment, primarily, of deep stabilizing muscles when performed correctly. If the deep muscle functions adequately, there is little activity of the superficial muscles. Conversely, if the deep muscle function is inadequate, the superficial muscle activity is increased. Monitoring of the superficial muscles may be combined with monitoring of the deep joint stabilizing muscle using ultrasound imaging (12) and/or pressure biofeedback. The apparatus includes an EMG unit (3) ultrasound unit, pressure biofeedback unit (16) and vitalograph (9), in combination with a computer (5) programmed to analyze data from them and given an indication of function.

35 Claims, 17 Drawing Sheets

135

136

137

MUSCLE FUNCTION ASSESSMENT APPARATUS AND METHOD

RELATED APPLICATIONS

This application is a continuation application of co-pending International Application No. PCT/AU98/00340, filed May 8, 1998, which designates the United States, and which claims priority of Australian Patent Application No. PO6739 filed May 9, 1997.

FIELD OF THE INVENTION

THIS INVENTION relates to the field of muscle function assessment and in particular the assessment of function of deep, joint stabilizing muscles.

BACKGROUND OF THE INVENTION

The causes of musculoskeletal pain include injury, degenerative joint disease and overuse injuries. Such pain affects the vast majority of the population at some time and in some form and may impact significantly on a sufferers quality of life and personal productivity. The generalised incidence and variable severity of such pain results in a significant cost for society.

Persistent musculoskeletal pain is increasingly identified as originating from joints as a result of poor muscle control of relevant muscles with associated poor joint stability. There is clear evidence linking restoration of stability of the joints with resulting pain control. Various muscles are used to protect and control any particular joint. Some are deep and close to the joint ("deep muscles") while others are often larger and further away from the joint but still exert an influence on the joint ("superficial muscles"). The joint stabilising function of these muscles can be divided into two basic components being the timing of muscle contraction and the manner of muscle contraction, particularly in relation to other muscles. As a result of the increasing awareness of causation of joint pain, its management has been directed towards improving the stabilising function of the muscle system and its ability to protect and support the joints. Various assessment, prevention and rehabilitation programmes have been implemented at considerable cost but with little systematic or objective appraisal of the results on joint stabilisation and efficacy in relieving pain. The main limiting problem in objective assessment of joint function and assessment of response to treatment is the absence of practical methods of in vivo assessment to enable evaluation of the stabilising capacity of the most relevant muscles. Some attempts have been made to address this deficiency.

Australian Patent AU 657277 describes a pressure biofeedback apparatus which permits monitoring of performance of physiotherapy exercises and enables the checking of compliance with prescribed instructions. The purpose is to ensure correct muscle action during exercise and also to ensure safety and precision of stretching techniques. While important in the described function, the device does not give a reliable indication of specific deep muscle function or the activity of such a deep muscle or muscles in relation to other muscles.

Use of pressure biofeedback monitoring with abdominal drawing in exercises is known. Similarly, pressure biofeedback has been used during abdominal drawing in exercises in lower back pain in combination with electromyographic ("EMG") biofeedback monitoring of the rectus abdominis and obliquus abdominis externus to confirm that the drawing in action is being produced by the deep abdominals with minimal activation of the large superficial muscles. (Richardson C A, Jull G A: An historical perspective on the development of clinical techniques to evaluate and treat the active stabilizing system of the lumbar spine. Australian Journal of Physiotherapy Monograph No 1 at 8, 1995) Use of this technique however requires a level of specialist training above that of an average practicing physiotherapist as the technique is prone to inaccuracies which can only be detected by subtle clinical signs. Clinical proficiency in assessing deep muscle function requires skills based on a knowledge of the principles of motor learning as well as skills to detect when substitution strategies are being used for an action.

U.S. Pat. No. 4,592,371 describes a simple pressure recording device to allow a gross measurement of pressure and duration created by the recruitment of large muscle masses such as an entire limb and is a basic indicator of large muscle group performance. It is of little use in deep muscle assessment.

WO 96/29929 discloses a diagnostic apparatus for the diagnosis of lower back pain which relies on comparison of the timing of contraction initiation in an anticipatory muscle and in a prime mover muscle. Use of the disclosed apparatus, however, relies principally on insertion of fine wire electrodes in the deep muscles of interest and comparison of muscle function is restricted to relative times. The clinician obtains an indication of muscle function and the technique is of great use in lower back pain but suffers from the disadvantage of its invasiveness.

Use of real-time ultrasound to view muscle contraction is known and has been used to provide biofeedback to both clinicians and patients. (Hides J A, Richardson C A, Jull G A, Davies S: Ultrasound imaging in rehabilitation, Australian Physiotherapy 41:187, 1995). This technique has the benefit of visualization of specific muscle contraction coupled with the ability to determine the duration of contraction. However, it does not provide an indication of the extent of utilization of other superficial muscles to the activity nor does it give a quantification of the contraction of the deep muscle.

Clearly there is a need for an apparatus or method of assessment which gives an objective measurement of the function of the muscular support of a joint or joints and which preferably is non-invasive. Such an apparatus or method could be used as an aid in diagnosing lack of stability, assessing the specificity of a remedial exercise programme and monitoring improvement subsequent to therapeutic invention. There is also a need for a non-invasive technique to assess the function of deep muscles without the requirement of specialized training of the operator.

OBJECT OF THE INVENTION

It is an object of this invention to provide an apparatus and/or method for use in assessing the function of muscular support of at least some joints which ameliorates some of the deficiencies of the prior art.

DISCLOSURE OF THE INVENTION

In one form but not necessarily the only or, indeed, the broadest form, the invention resides in an apparatus for assessing the function of deep muscle comprising:

means for establishing signals indicative of a baseline level of activity of at least one superficial muscle;

monitoring means to monitor activity of at least one superficial muscle and produce signals characteristic of muscle activity;

display means to display said signals indicative of a baseline level of activity and said signals characteristic of muscle activity of at least one superficial muscle; and analysis means to analyse said signals indicative of a baseline level of activity in relation to said signals characteristic of muscle activity of at least one superficial muscle to produce an indicator of deep muscle function.

Preferably the means for establishing signals indicative of a baseline level of activity and the means for monitoring superficial muscle activity are an EMG means. Alternatively, the means for establishing signals indicative of a baseline level of activity and the means for monitoring superficial muscle activity are an ultrasound imaging means. EMG means and ultrasound imaging means maybe used in combination.

Preferably said display means is an oscilloscopic screen. Alternatively, said display means may be a trace recording or other suitable means.

Said analysis means may be a user with skills to observe and interpret the signals shown on the display means. Alternatively, said analysis means may be a processing means. Suitably the processing means is a processor programmed to perform an algorithmic function on the signals provided by said means for establishing a baseline level and said monitoring means by reference to said baseline level of activity and said superficial muscle activity wherein the algorithmic function is based on the formula:

$$a(t) \propto \frac{1}{m-b}$$

where:

a is the function of the deep muscle, t is the time of contraction m is the activity of the superficial muscle; and b is the baseline activity of the superficial muscle.

Preferably, the processing means is in signal connection with said means for establishing a baseline level of activity and said monitoring means for the superficial muscle and is adapted to receive and translate said signals indicative of a baseline level of activity of at least one superficial muscle and said signals characteristic of superficial muscle activity, to an indication of deep muscle function according to an algorithm of the form:

$$a(t) \propto \frac{1}{m-b}$$

Suitably the apparatus further comprises means for monitoring change in force exerted by muscles. Preferably, said means for monitoring change in force monitors change in pressure which characterizes the activity of the deep muscle and is in signal connection with the processing means. The means for monitoring change in pressure may be a pressure biofeedback unit. Preferably the signals from the means for monitoring change in pressure are relayed to the processors which is programmed to perform an algorithmic function wherein if p is between p1 and p2, where p1 is a level of the monitored pressure recorded when the subject is at rest and p2 is a set limit of the monitored pressure and p is the pressure recorded during the performance of an activity; then a ΔP where ΔP is the difference between p1 and p.

It will be evident that the means for monitoring change in force and the monitoring means for the superficial muscle can be used conjunctively.

Alternatively, said means for monitoring change in force may be a means to monitor variation in spinal orientation and position wherein said variation characterises the activity of the deep muscle.

Preferably the apparatus further comprises visualising means to view at least one deep muscle. Suitably said visualising means is an ultrasound imaging unit. Alternatively, the visualizing means may be a magnetic resonance imaging apparatus, computed tomography unit or other appropriate visualising means.

In preference, the apparatus further comprises a means for establishing a substantial level of activity of at least one superficial muscle. Suitably the means for establishing a substantial level of activity is a vitalograph. Alternatively, the means for establishing the substantial level of superficial muscle activity level may further or separately utilize a pressure biofeedback unit or other suitable apparatus. Said means for establishing a substantial level of activity is in signal connection with said processor. The processor is programmed to apply an algorithm in which:

$$a(t) \propto \frac{s-b}{m-b}$$

where: s is the substantial level of activity of a superficial muscle as detected by the superficial muscle monitoring means.

In one form, signal connection between said means for establishing a substantial level of activity of the superficial muscle and the processor requires an operator to enter data obtained from said means for establishing a substantial level into the processor by an input device.

In a further form, the invention resides in a method of assessment of the function of at least one deep muscle of a subject including the steps of:

(i) establishing a baseline level of activity of at least one superficial muscle;

(ii) monitoring the activity of the superficial muscle;

(iii) the subject performing at least one prescribed activity;

(iv) analysing the activity of the superficial muscle during the prescribed activity and the baseline level of activity to produce an indication of function of the deep muscle; and (iii) displaying the indication on a display means.

Suitably, the baseline activity of at least one superficial muscle is obtained by monitoring the muscle at rest. Preferably the monitoring of the muscle is achieved through use of EMG means. Alternatively, the means for establishing signals indicative of a baseline level of activity and the means for monitoring superficial muscle activity are an ultrasound imaging means.

The prescribed activity is an exercise known to require substantial contraction of a deep muscle under assessment when performed correctly.

Preferably the method includes the further step of monitoring the activity of the deep muscle of the subject simultaneously with monitoring the activity of the superficial muscle. Suitably the monitoring of the activity of the deep muscle is by visualizing means. The visualizing means is suitably ultrasound imaging. Alternatively, computed tomography or magnetic resonance imaging or other appropriate visualizing means may be used. Alternatively, the monitoring of the deep muscle may be performed using pressure monitoring means. The pressure monitoring means is suitably a pressure biofeedback unit. Alternatively, the monitoring of the deep muscle may be by a combined use of visualizing means and pressure monitoring means.

In preference, the method further includes the step of establishing a substantial level of activity of the superficial muscle.

Suitably the substantial level of activity is obtained by monitoring the superficial muscle while the subject performs an exercise known to require substantial input from the superficial muscle. Preferably monitoring of the superficial muscle is by the use of EMG means. The steps of establishing a baseline level of activity or establishing a substantial level of activity may be performed before or after the subject performs the prescribed activity. Alternatively, the means for establishing signals indicative of a baseline level of activity and the means for monitoring superficial muscle activity are an ultrasound imaging means.

The analysis may be performed by a trained clinician. Alternatively, the analysis is performed using processor means. In the preferred embodiment, the processor means is a computer. The analysis may include application of an algorithm to variables which may include comparison of substantial superficial muscle activity, baseline superficial muscle activity and superficial muscle activity during the prescribed activity, duration of deep muscle contraction, force of deep muscle contraction, pattern of deep muscle contraction and degree of isolation of deep muscle contraction. Alternatively, the analysis may require combination of some or all of the described variables.

Preferably the method involves the further steps of:
(1) varying the position of the subject and varying the activities performed by the subject;
(2) monitoring superficial muscle activity during said activities;
(3) monitoring the deep muscle activity during said activities;
(4) identifying in which positions or during which activities deep muscle use is maximal or significant; and
(5) selecting exercises for deep muscle strengthening based on the identification.

BRIEF DETAILS OF THE DRAWINGS

To assist in understanding the invention preferred embodiments will now be described with reference to the following figures in which.

DETAILED DESCRIPTION OF THE DRAWINGS

Figure 1:
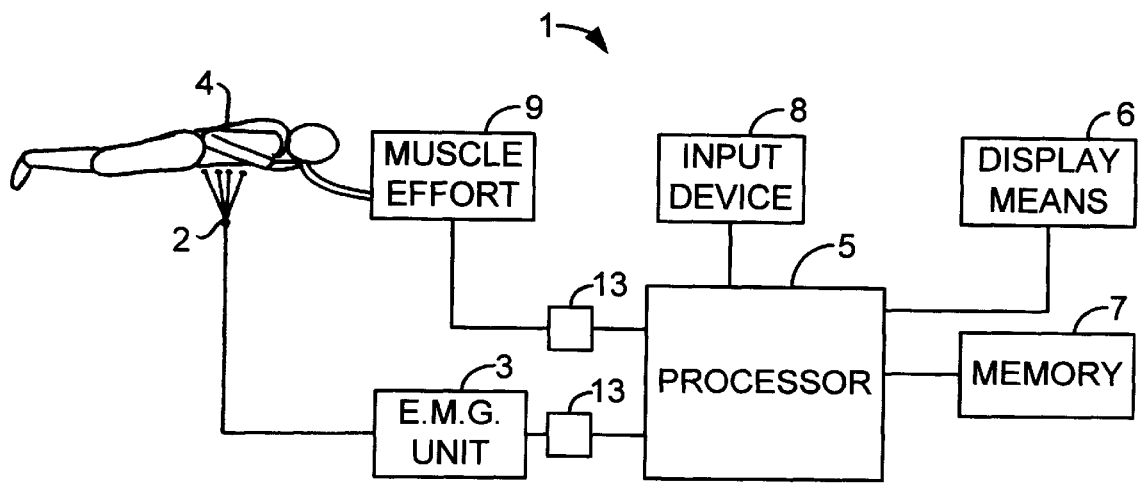
FIG. 1 is a block schematic diagram of a first embodiment of an apparatus for assessing the function of deep muscles.

FIG. 1 is a block schematic diagram of a first embodiment of the deep muscle assessing apparatus 1 comprising an EMG unit 3 and processor 5. Skin electrodes 2 of the EMG unit 3 are in signal connection with a subject 4. The EMG unit 3 is in signal connection with the processor 5 which has display means 6 and memory means 7. An input apparatus 8 may be provided for input of data or programming of the processor 5. A superficial muscle effort indicator 9 is in signal connection with the processor 5. Digitizers 13 are in signal connection with the EMG unit 3 and muscle effort indicator 9 and convert analogue signals to digital signals. The signals are then relayed to the processor 5 which is in signal connection with the digitizers 13.

In use, a base line is established by recording the myographic activity of a selected superficial muscle or muscles of the subject 4 at rest.

The subject 4 then attempts an exercise specifically chosen because the contraction required for proper performance of the exercise is predominantly provided by the deep muscle/s of interest.

The superficial muscle/s are monitored during the performance of this later exercise. Electrical activity of the superficial muscle/s is ascertained by the EMG unit 3 and information is passed to the processor 5 where it is analyzed by application of an algorithm in which $$a(t) \propto \frac{1}{m-b}$$

where:
a is the function of the deep muscle,
t is the time of contraction
m is the activity of the superficial muscle; and
b is the baseline activity of the superficial muscle.

The processor 5 produces a quotient which is an indication of the function of the deep muscle.

Optionally, an enhanced level of accuracy may be obtained by including the following steps. The subject 4 attempts an activity which is known to require the superficial muscle/s of interest to contract in a substantial manner. This activity may be repeated several times and muscle activity is monitored by the EMG unit 3 which relays signals to the processor 5 where the signals are recorded and analyzed to establish a level of substantial activity for the particular superficial muscle/s in that subject. Signals received by the processor during performance of the exercise chosen for deep muscle recruitment are analyzed with the signals from substantial contraction of the superficial muscles according to an algorithm to produce a quotient. A suitable algorithm is of the form:

$$a(t) \propto \frac{s-b}{m-b}$$

where: s is the substantial level of activity of a superficial muscle as detected by the superficial muscle monitoring means.

The memory 7 may include a database in which is stored a range of results generated from testing a large number of subjects who together display a representative range of deep muscle function for the deep muscle/s under assessment. The processor 5 may be programmed to compare the quotient with information from the database to further categorize the function of the deep muscle under assessment. In a further preferred embodiment, information from the subject under assessment is added to the database.

In a modification of the first embodiment of the invention, a baseline level of the superficial muscle is obtained by EMG monitoring. The baseline level is compared with a database derived standard for a population to create a conversion factor that normalizes the measurements. An absolute measurement is made of the superficial muscle during prescribed activities selected to recruit the deep muscle under assessment. This measurement is multiplied by the conversion factor to create a product which is compared against a standard scale to give an indication of function of the deep muscle.

Analysis and categorization results from the inventors' discovery of the inverse relationship between superficial muscle and deep muscle activity and the application of that knowledge to results obtained from monitoring muscles during selected activities or from application of multiple methods of examination of muscles used simultaneously.

The result is then displayed by the deep muscle assessing apparatus 1 on display means 6 in any appropriate fashion such as illumination of one of a set of indicator bulbs 11 (shown in FIG. 2), display on a scale or other representation which is meaningful to a clinician.

An assessment of the transversus abdominis, a deep stabilizing muscle of the lumbar spine, will now be described by way of example. Skin electrodes 2 are applied to monitor the electrical activity of the following superficial muscles: abdominis obliquus externus, abdominis obliquus internus, rectus abdominis and erector spinae. A base line measurement is taken at rest with the subject 4 in a prone lying position. The subject 4 then performs forced expiration into the superficial muscle effort indicator means 9, which in this case is a vitalograph. Results detected by the vitalograph are converted into digital information by the digitizer 13 and relayed to the processor 5 which also signals the processor 5 to monitor signals from the EMG unit 3. Signals from the EMG 3 and vitalograph 9 are analyzed to establish an upper limit of the superficial muscle activity for the purposes of assessment.

The subject 4 then attempts an appropriate exercise such as abdominal drawing in which, in correct performance, is predominantly achieved by contraction of the transversus abdominis in isolation from the superficial muscles. If the deep muscle is fully functional, little activation will occur in the monitored superficial muscles while the deep muscle will contract strongly and persistently which will be reflected in a quotient falling within a normal range of the spectrum established in the database. Conversely, if the deep stabilizing muscle is deficient in its function, the subject automatically attempts to substitute for the dysfunction of the deep muscle with contraction of the monitored superficial muscles which results in greater activity in the EMG recording. Analysis of results will produce a quotient which falls in a range of the database indicating dysfunction.

Figure 2:
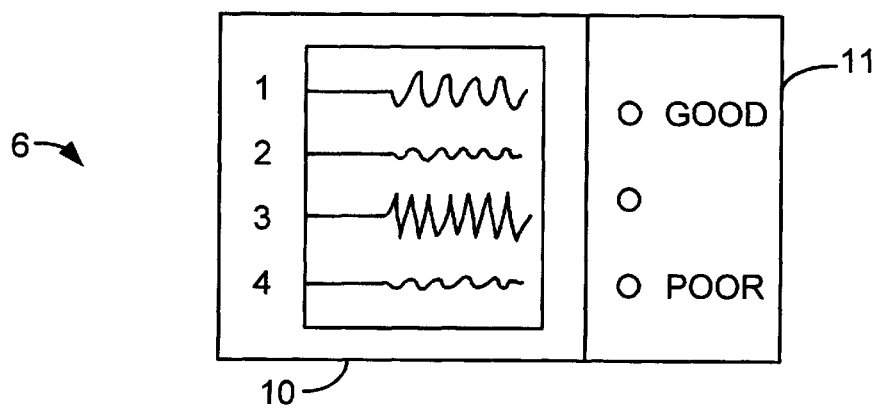
FIG. 2 is a diagram of a display screen of the apparatus of FIG 1.

FIG. 2 is a diagram of a display means 6 with a visual oscilloscopic representation of the EMG activity and a simultaneous indication of function 11 of the deep stabilizing muscle under investigation after analysis by the processor 5.

Figure 3:
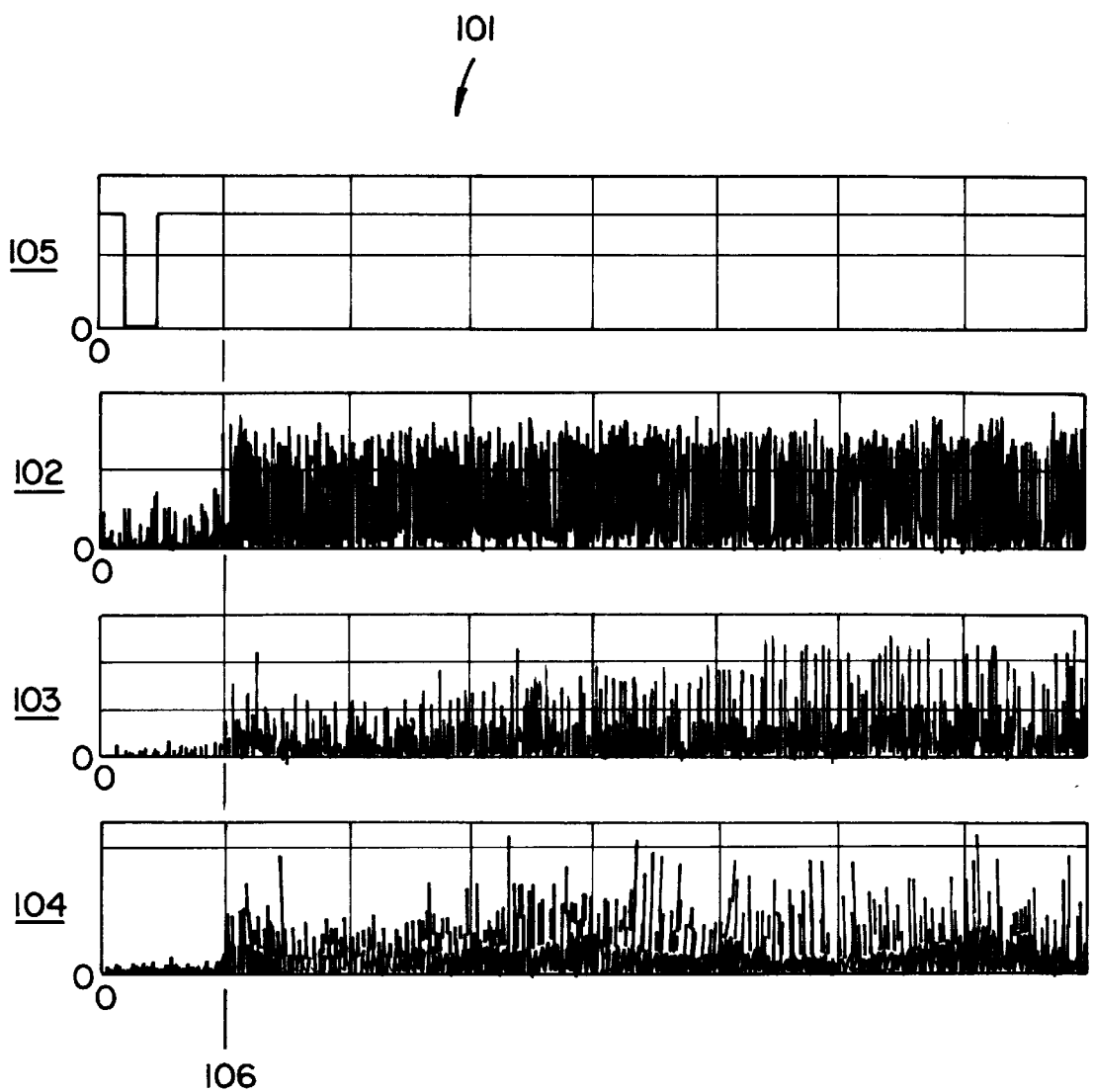
FIG. 3 is an EMG trace for three superficial muscles of the lower back.

FIG. 3 shows simultaneous EMG traces 101 from three (3) superficial muscles of the lower back, as seen on the screen shown in FIG. 2. A first trace 102 is of signals received from the abdominis obliquus internus. A second trace 103 is of signals received from the abdominis obliquus externus. A third trace 104 displays signals received from the rectus abdominis. A baseline recording of activity is obtained prior to the commencement of a prescribed activity. The commencement of such prescribed activity is represented by a recording of a commencement signal 105 and by the line 106 on the EMG tracings 101. Tracings preceding the line 106 represent a baseline activity and the tracings which follow the line 106 represent activity of the superficial muscles during a prescribed activity.

The EMG tracings can be further analysed by calculating the Root Mean Square (RMS) value. The RMS is calculated using the following formula:

$$RMS\{m(t)\} = \left(\frac{1}{T}\int_{t}^{t+\omega} m^{\theta}(t)dt\right)^{1/2}$$

where: m is the magnitude of the signal at time t and the integration is made over period T.

A high RMS value is indicative of high superficial muscle activity and correlating poor deep muscle activity. The converse is also true.

Figure 4:
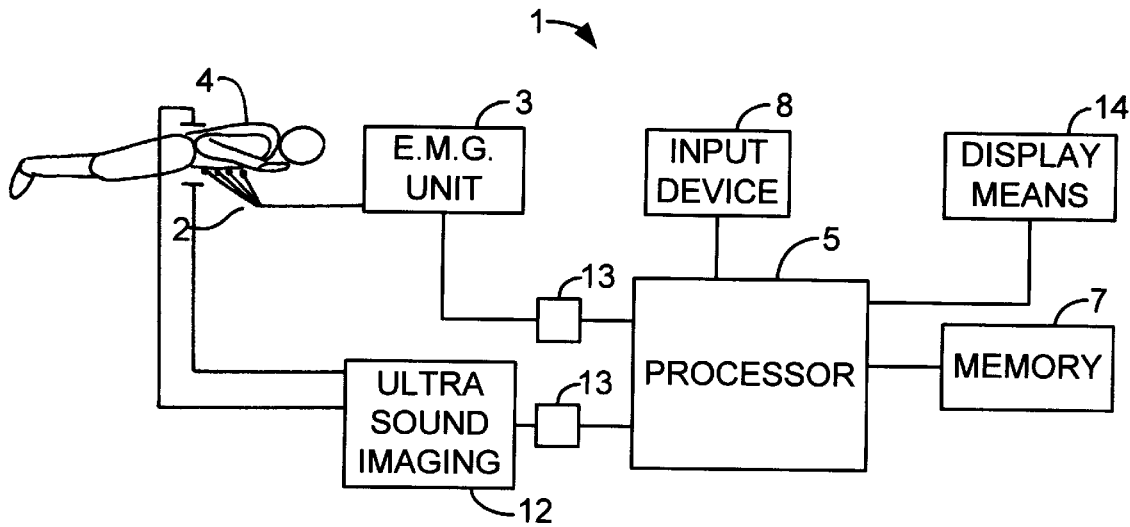
FIG. 4 is a block schematic diagram of a second embodiment of an apparatus for assessing the function of deep muscles.

FIG. 4 is a block schematic diagram of an embodiment of the invention incorporating the features of FIG. 1 (with the exception of superficial muscle indicator 9) and an ultra sound imaging unit 12 with digitizer 13. The digitizer 13 sends digital information to the processor 5 recording various indicia of the deep muscle of interest which may include timing and duration of the muscle contraction, movement of the muscle borders relative to each other and movement of the deep muscle relative to other anatomical landmarks external to the muscle. A touch screen (not shown) may be included in the apparatus to permit a clinician to electronically mark a position on the ultrasound image of the deep muscle before and during contraction for quantification of muscular movement.

Signals from the ultrasound 12 and EMG unit 3 are subject to analysis by the processor 5 by application of an algorithm to display an indication of the function of the deep stabilizing muscle. The algorithm may utilize time and intensity of contraction and movement of the deep muscle, and intensity of the contraction of the superficial muscle/s as recorded by the EMG unit 3, as data. The intensity of the contractions of the superficial muscle/s as indicated by the EMG recording is inversely related to the function of the deep muscle.

An assessment of the transversus abdominis, a deep stabilizing muscle of the lumbar spine is described by way of example. A patient is placed in a prone lying position. Skin electrodes 2 of an EMG unit 3 are applied in standard positions to monitor the following muscles: abdominis obliquus externus, abdominis obliquus internus, rectus abdominis and erector spinae. An operator locates the head of the ultra sound unit 12 so as to display the transversus abdominis at a standard anatomical location which is checked by visual reference to the display means 14. The subject 4 then performs a standard activity which requires the recruitment of all superficial muscles under monitoring. In this example, that exercise may suitably be forced expiration. After several repetitions, a level of EMG activity is calculated by the processor 5 which is related to a base line minimal level of activity taken when the subject is at rest.

The subject then attempts an exercise which, when correctly executed, requires substantial or total contribution from the transversus abdominis. The exercise may be, for example, abdominal drawing in. On commencement of the selected exercise, a measurement is taken by a lateral border movement monitor (not shown) which detects and monitors the diameter of the transversus abdominis in the region of a selected standard anatomical location. During contraction of the muscle, relative movement may occur between muscle borders and movement of the borders may occur relative to external anatomical landmarks. Information relating to the variation in diameter, duration of contraction and movement of the muscle is relayed to the processor 5 and subject to analysis with all other information received to provide an indication of the function of the transversus abdominis.

Figure 5:
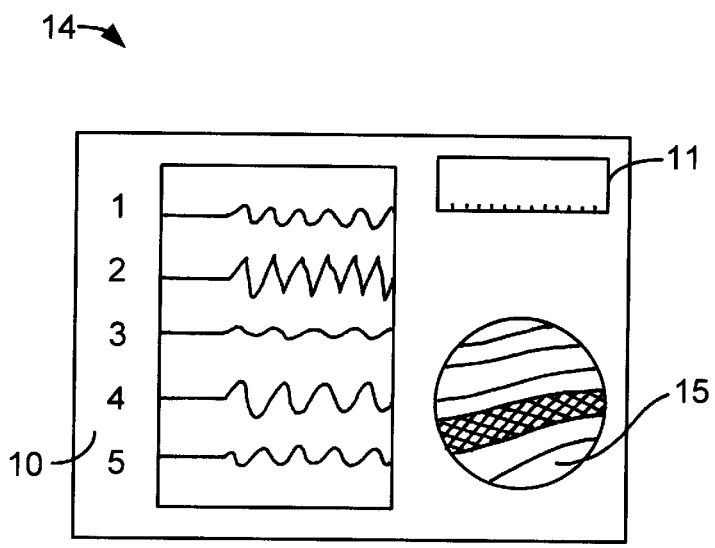
FIG. 5 is a diagram of a display screen of the apparatus of FIG. 3.

FIG. 5 is a representation of the display means 14 with an oscilloscopic representation 10 of the EMG activity, an indicator of function 11 and an ultrasound display screen 15.

Figure 6:
FIG. 6 is an ultrasound image in transverse section of the abdominal wall at rest.

FIG. 6 is an ultrasound image in transverse section of the abdominal wall at rest recorded by the apparatus of FIG. 4. The image displays the skin 107, subcutaneous tissue 108, the abdominis obliquus externus 109, the abdominis obliquus internus 110 and the transversus abdominis 111.

Figure 7:
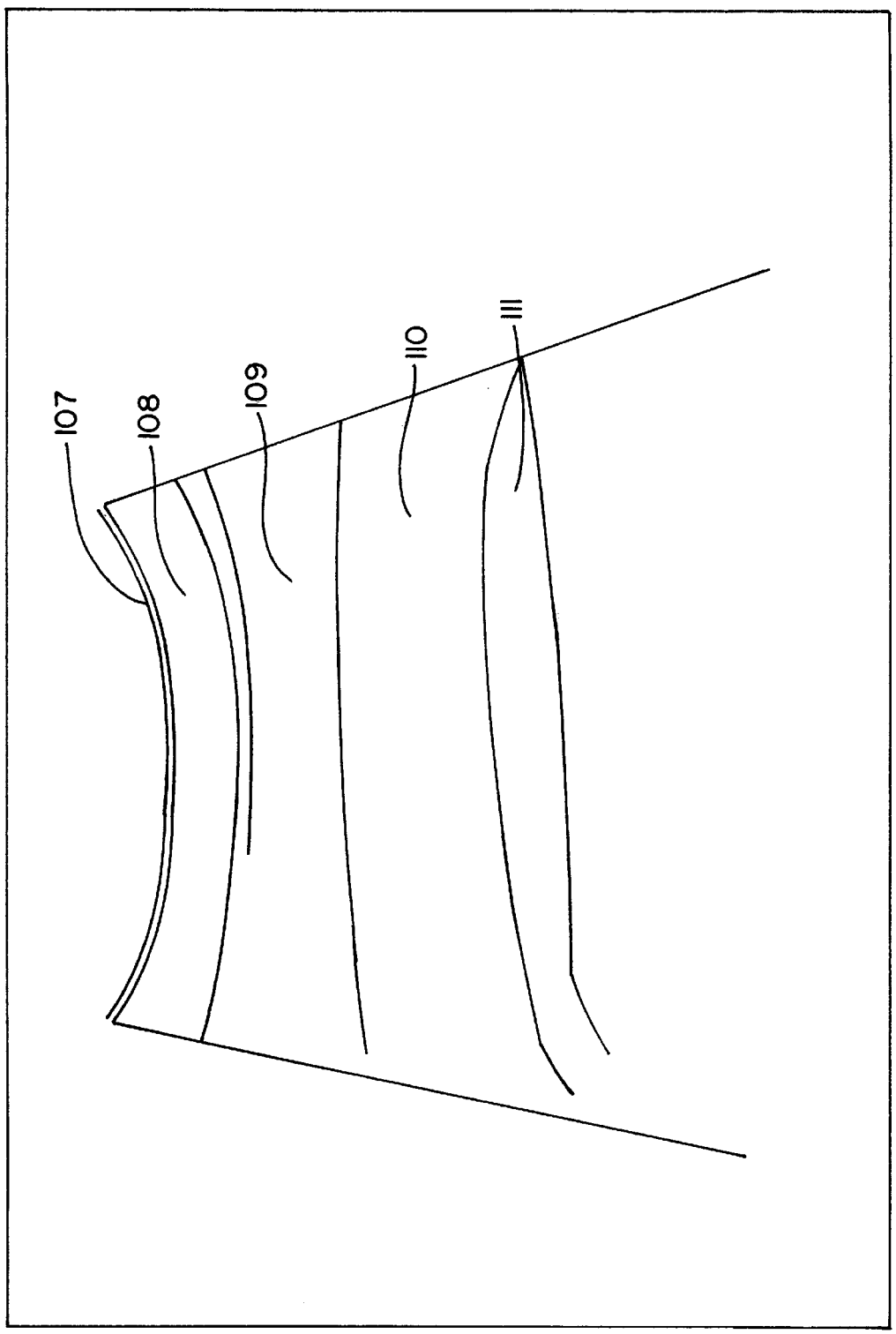
FIG. 7 is a schematic representation of the ultrasound image of FIG. 6.

The same structures are represented schematically in FIG. 7 with the same numbering.

Figure 8:
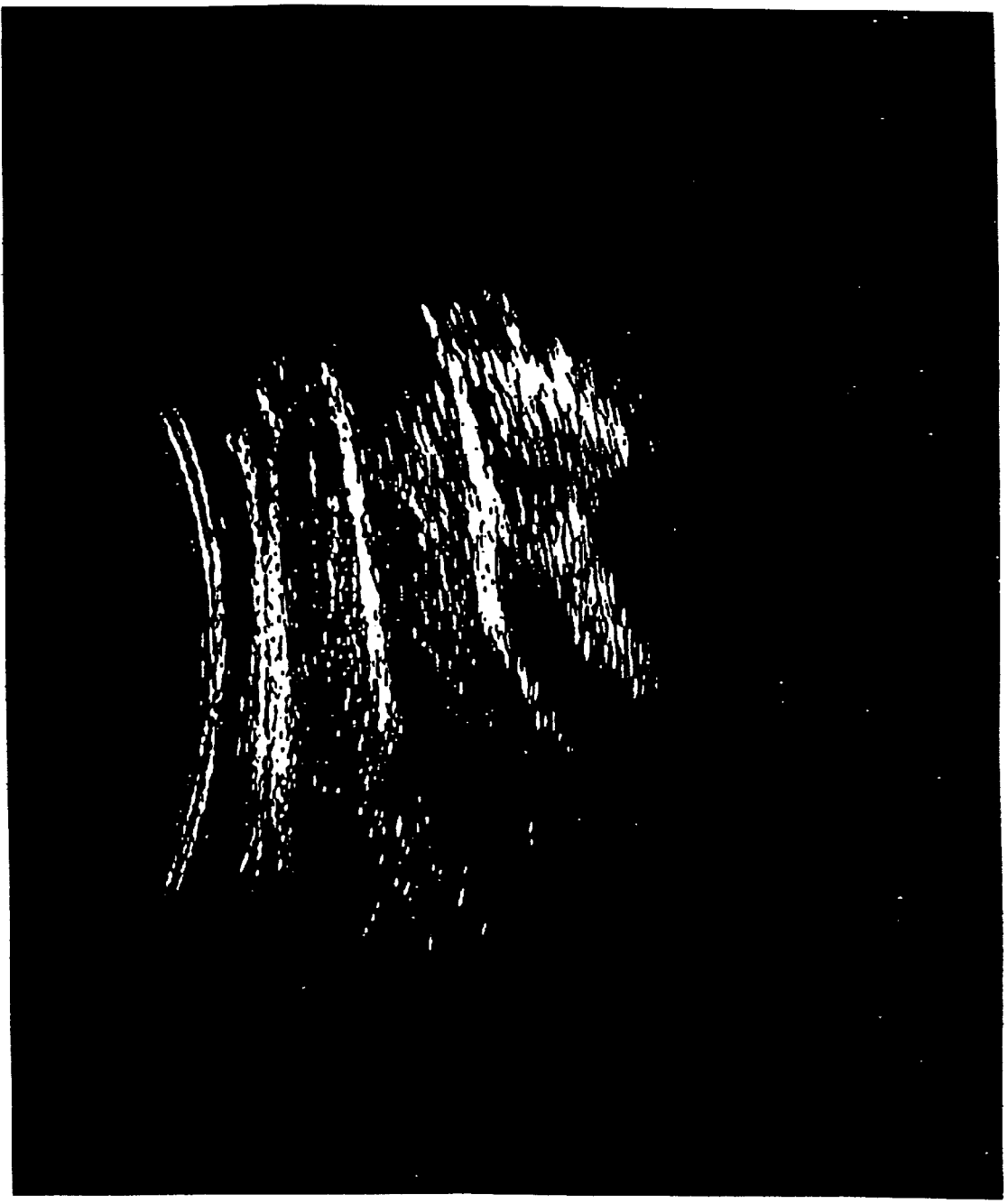
FIG. 8 is an ultrasound image of the abdominal wall in transverse section following performance of the abdominal drawing in action.

In FIG. 8, the same features as in FIG. 6 are seen but monitored during the performance of the abdominal drawing in action. The image displays the skin 112, subcutaneous tissue 113, abdominis obliquus externus 114, abdominis obliquus internus 115 and transversus abdominis 116.

Figure 9:
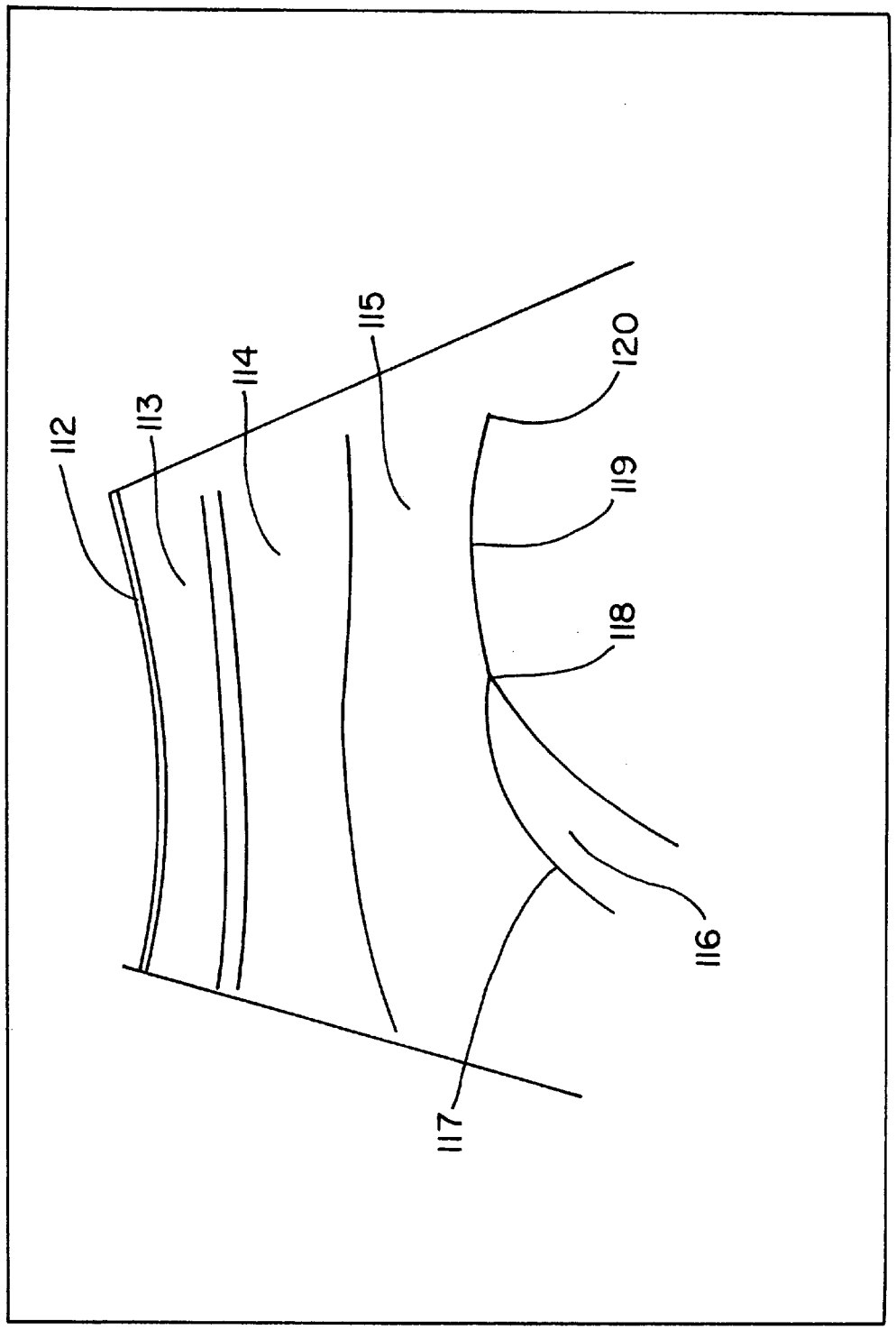
FIG. 9 is a schematic representation of the ultrasound image of FIG. 8.

The same features are represented schematically in FIG. 9 with the same numbering.

FIGS. 6 to 9 show changes during the performance of abdominal drawing in by a subject competent in its performance, as viewed on the apparatus of the invention. The transversus abdominis 111, 116, displays increased transverse dimensions as a result of contraction. That contraction is an indication of its function as is the period during which contraction is sustained.

The function of the transversus abdominis may be further considered with reference to the curvature of the muscle during contraction on its margin 117, the displacement of the medial attachment 118 of the transversus abdominis to fascia 119 and elongation of the fascia 119 during contraction.

An objective of measurement of the alteration of the transversus abdominis may be obtained by use of touch screen markers at a specific anatomical point such as the medial attachment 118 of the transversus abdominis 116 to fascia 119 or to a point on the midline fascial attachment 120. The displacement of the marker provides an indication of muscle activity. The indicator is converted to an absolute measurement with appropriate conversion factors.

Alternatively, the measurement may be carried out automatically by the use of a Doppler shift monitor included in the apparatus of the invention. The Doppler shift monitor detects the frequency shift caused in the reflected ultrasound signal by the moving muscle.

Figure 10:
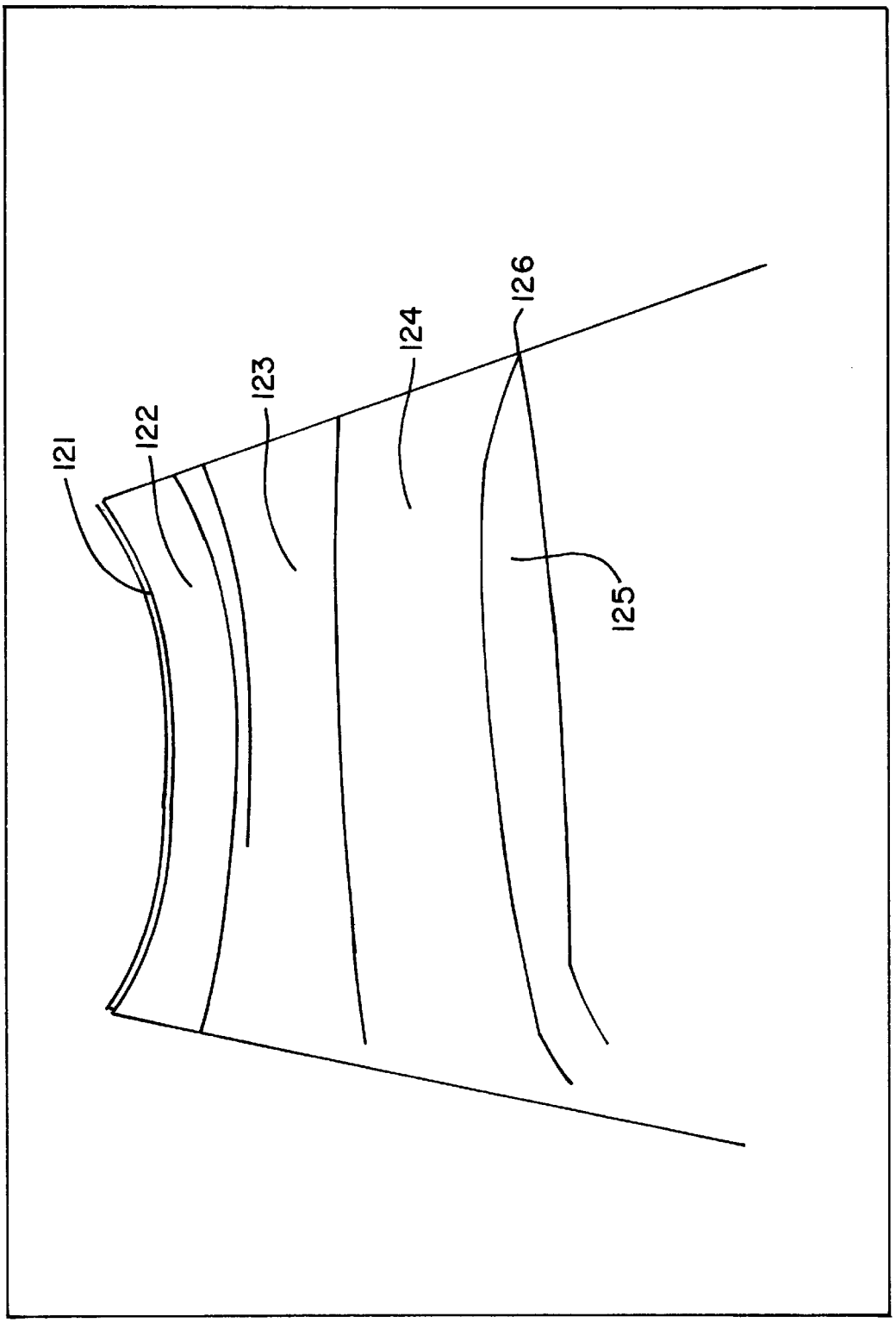
FIG. 10 is a schematic representation of an ultra sound image of an abdomen at rest.
Figure 11:
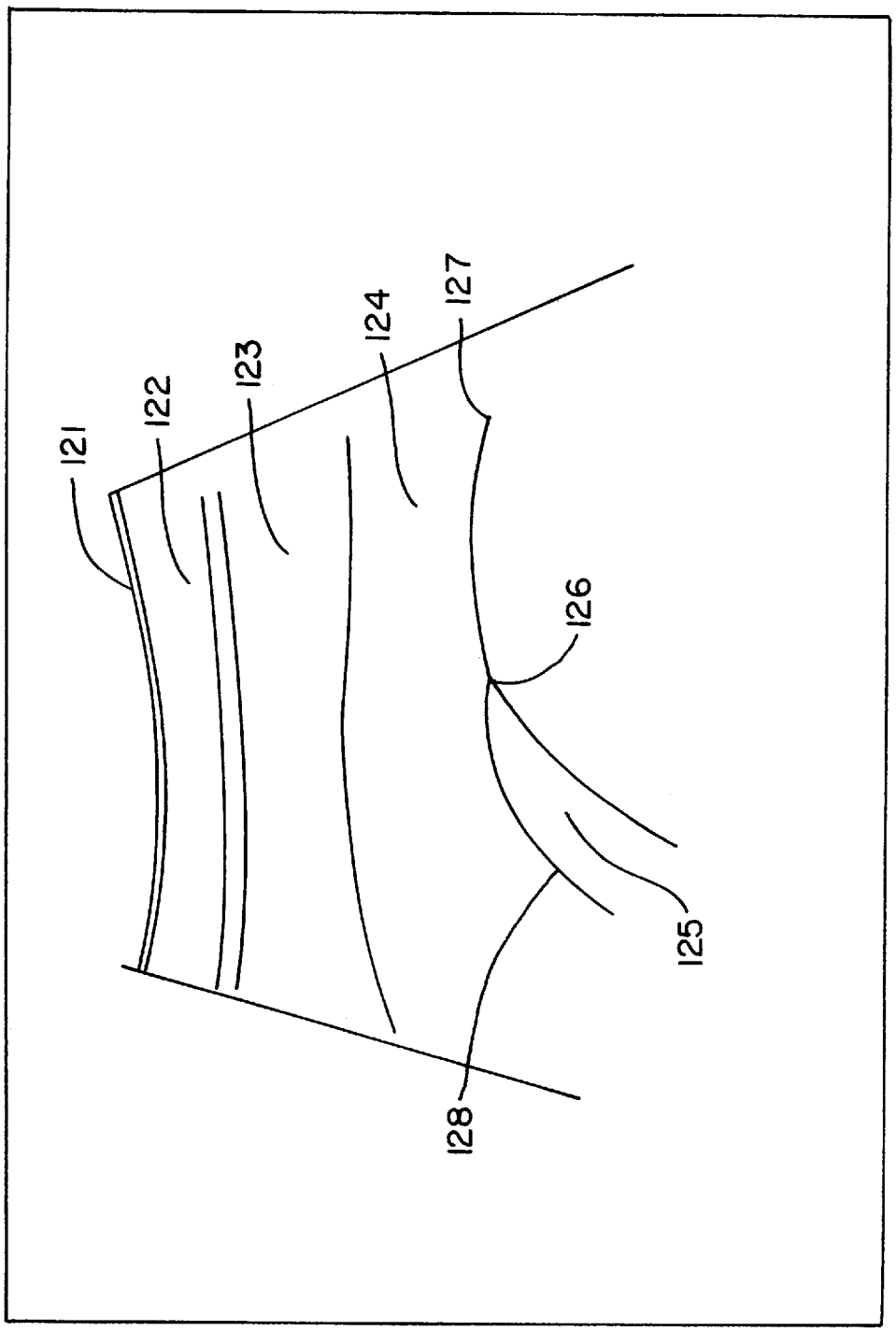
FIG. 11 is a schematic representation of abdominal muscles during correct performance of the abdominal drawing in action.
Figure 12:
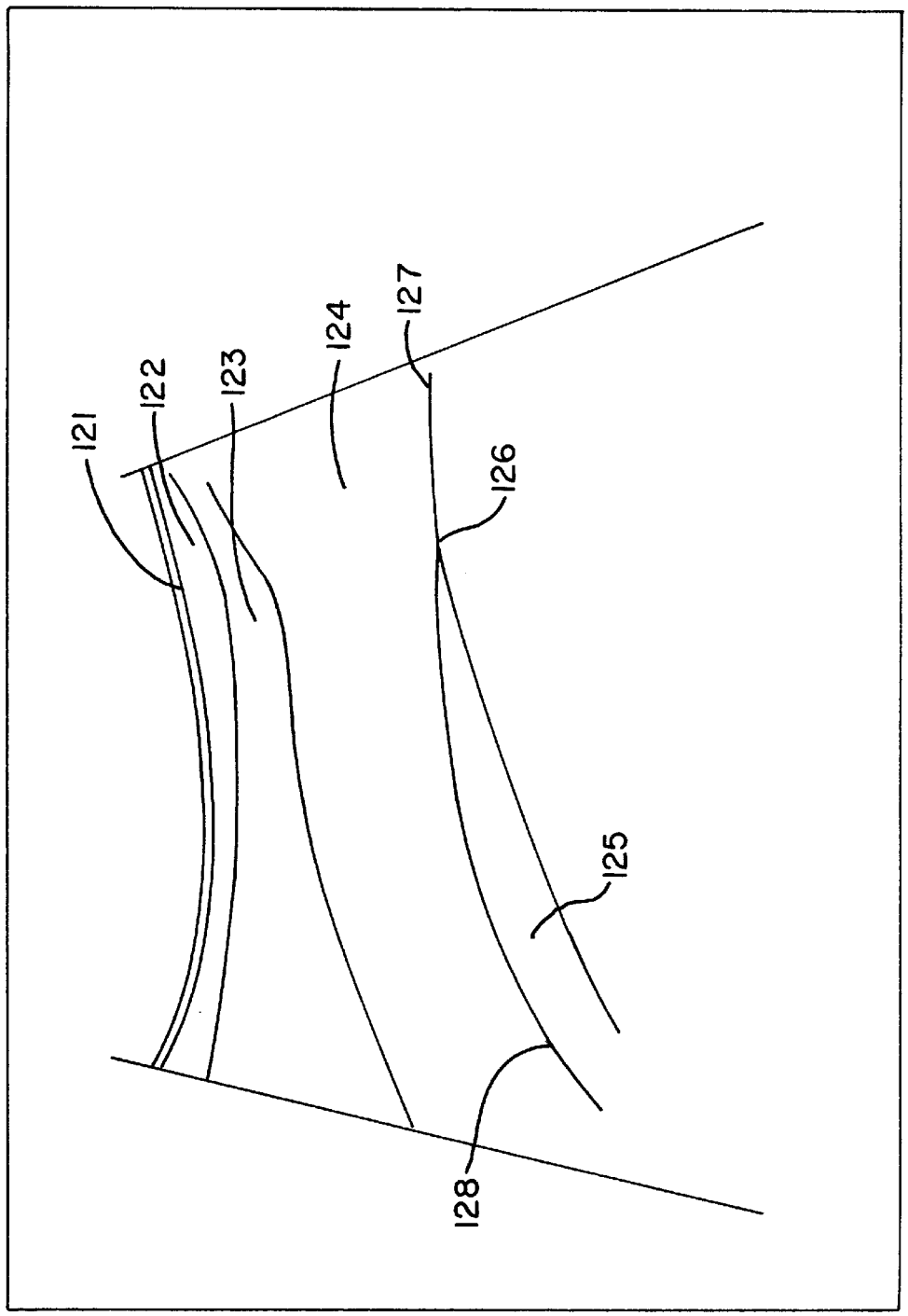
FIG. 12 is a schematic representation of abdominal muscles during incorrect performance of the abdominal drawing in action.

FIGS. 10, 11 and 12 display the differences between an abdomen at rest and during performance of a correct and incorrect drawing in action.

FIG. 10 is a schematic representation of an ultrasound image of an abdomen at rest in which is visible the skin 121, subcutaneous tissue 122, abdominis obliquus externus 123, abdominis obliquus internus 124 and the transversus abdominis 125. The medial attachment of the transversus abdominis 126 is located towards the midline of the subject (not shown). It can be seen that the transversus abdominis is a long and relatively thin muscle at rest.

FIG. 11 is a schematic representation of an ultrasound image of the same muscles during correct performance of the drawing in action. On contraction of the transversus abdominis, the muscle increases in depth and tensions the fascia 127 which attaches to the rectus abdominis. There is little change in the superficial muscles 123, 124. The transversus abdominis displays pronounced curvature along its border 128. The medial attachment 126 moves laterally (as shown) and downward (i.e. towards the abdominal cavity). Contraction of the muscle results in elongation of the fascia 127.

FIG. 12 is a schematic representation of an ultrasound image of an abdominal wall following incorrect performance of the drawing in action. There is an increased depth of the abdominis obliquus externus 123 and abdominis obliquus internus 124. Although, the transversus abdominis 125 shows an increase in thickness due to some contraction, it has less contribution to the drawing in action and its isolated activation is lost. There is less curvature of the border 128. The medial attachment 126 is only slightly displaced and there is decreased elongation of the fascia 127.

Figure 13:
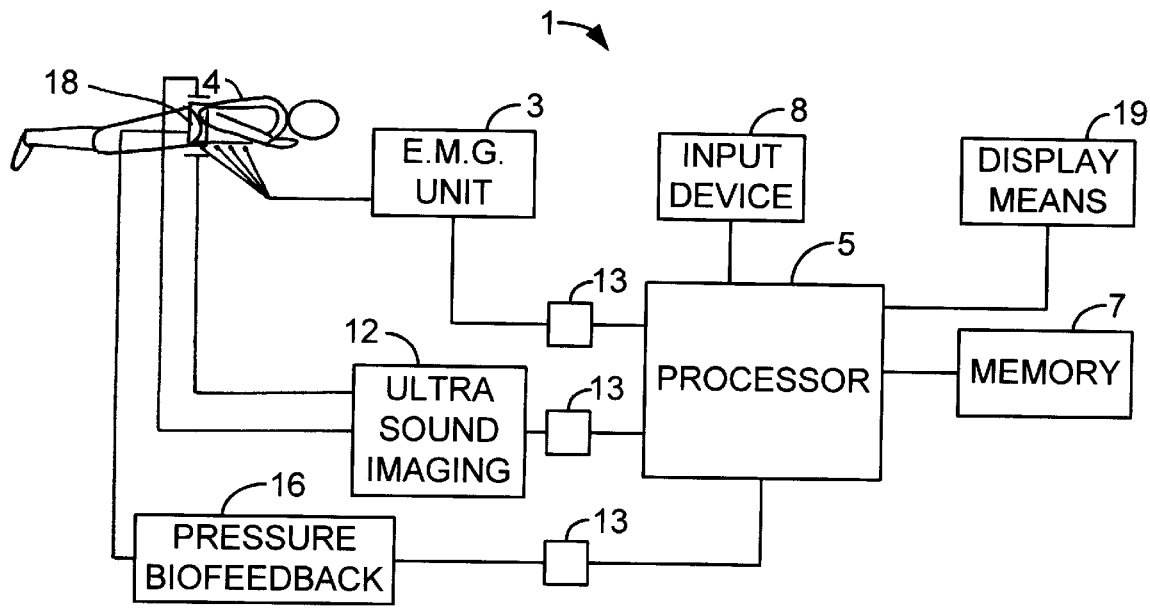
FIG. 13 is a block schematic diagram of a third embodiment of an apparatus for assessing the function of deep muscles.

FIG. 13 is a block schematic diagram of an embodiment of the deep muscle assessing apparatus of the invention which includes the features previously described in FIG. 3 with the additional features described below.

A pressure biofeedback unit 16 is incorporated into the deep muscle assessing apparatus of the invention which also has instruction indicators 17. In use, the instruction indicators 17 are activated by the processor and serve to direct the subject 4 to the three states of READY, START and STOP thereby allowing a set time to be used in any one or more activities. The processor 5 includes a timing apparatus such as a clock. The pressure biofeedback unit 16 provides a means, in combination with EMG and ultrasound monitoring of quantifying and monitoring the quality of deep muscle contraction.

In use, for assessment of the transversus abdominis the steps described for the embodiment shown in FIG. 3 are undertaken with the following additions. The clinician selects a duration for the performance of any requested exercise and programs that time into the deep muscle assessing apparatus. Alternatively, a standard time may be pre-set in the apparatus.

The subject 4 is placed in the prone lying position and a pressure pad 18 of the pressure biofeedback unit 16 is placed under the subject's abdomen. On performance of an appropriate exercise such as abdominal drawing in, the pressure recorded by the pressure biofeedback unit 16 should drop if the exercise is performed properly. The amount of decrease in pressure and its duration are indicative of the strength of the deep muscle/s contraction and the subject's ability to instigate that contraction. A usual decrease of six (6) to ten (10) mm of mercury maintainable for a period of ten (10) seconds for ten (10) repetitions is considered indicative of good muscle function. A large decrease in pressure may be indicative of poor performance as it indicates substitution of the action of other muscles for that of the transversus abdominis. Information from the pressure biofeedback unit 16 is digitized by a digitizer 13 and supplied to the processor 5 where it is subjected to analysis by application of an algorithm in combination with information from the ultrasound unit 12 and EMG unit 3 to provide an indication of the function of the transversus abdominis wherein:

$$a \Delta P$$

Figure 14:
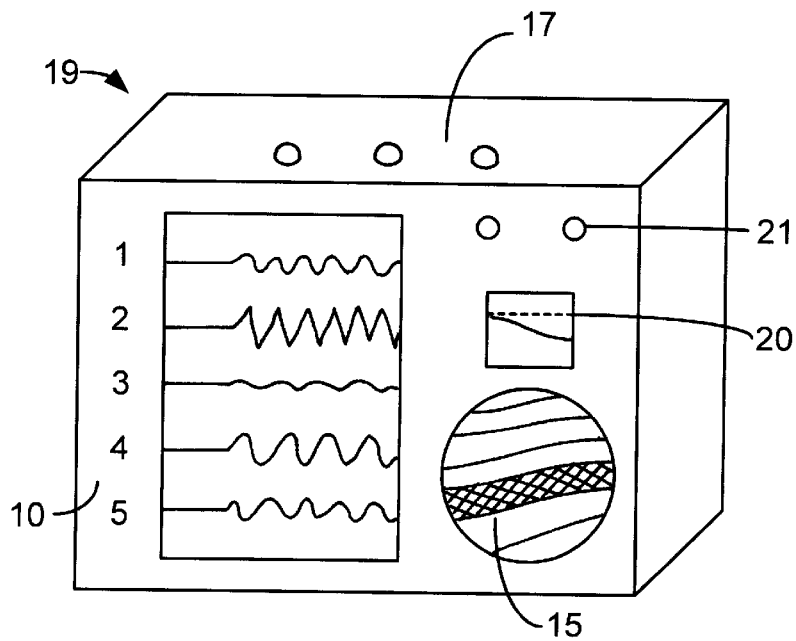
FIG. 14 is a diagram of the display screen of the apparatus of FIG. 5.

FIG. 14 is a diagram of the display means 19 with an oscilloscopic display 10 of EMG activity, an ultra sound display unit 15 and a pressure biofeedback display 20. The display means 19 also features instruction indicators 17 and muscle function indicator bulbs 21 which are illuminated to indicate the quotient calculated by the processor 5 which is classed as GOOD or POOR when compared with a range of results contained in a database stored in the memory 7 of processor 5.

Figure 15A:
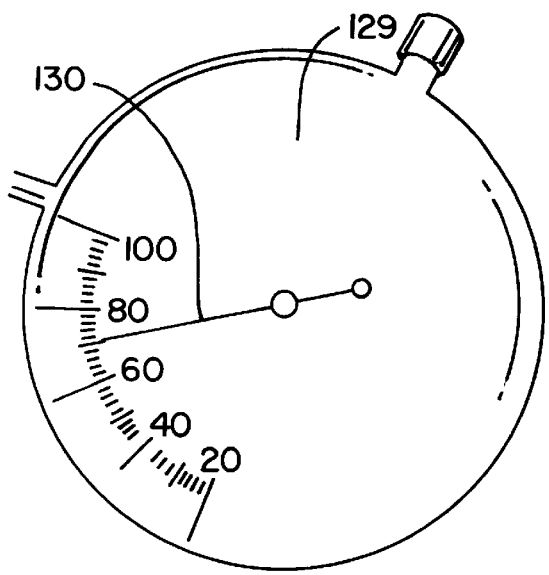
FIG. 15 shows simultaneous readings of the muscle function assessment apparatus attached to a subject at rest.
Figure 15B:
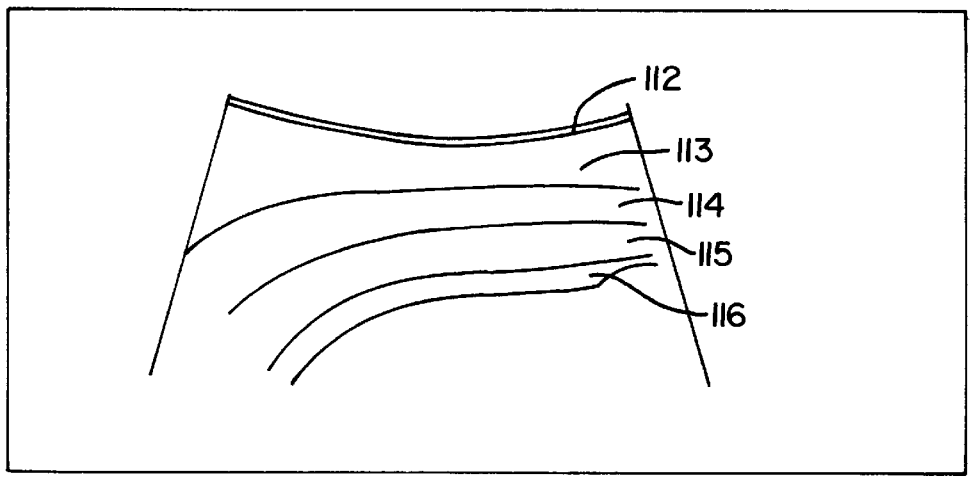
Figure 15C:
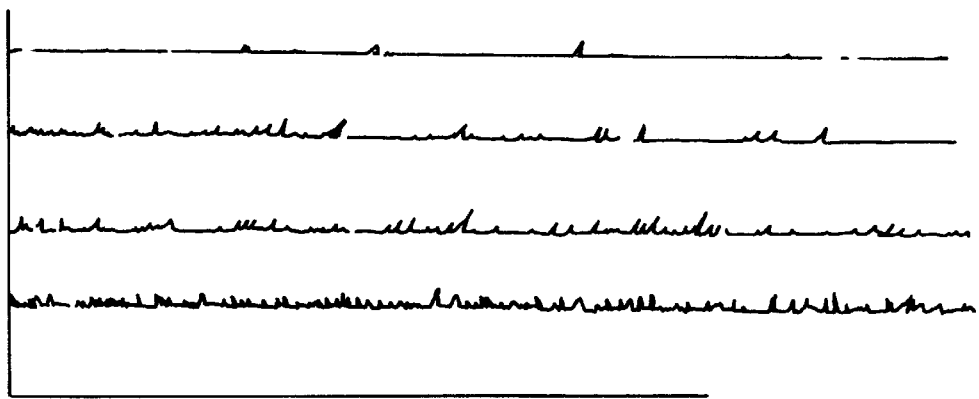

FIG. 15 shows simultaneous readings of the muscle function assessment apparatus for pressure biofeedback, ultrasound (schematic) and EMG (schematic).

A pressure biofeedback monitor 129 of the apparatus indicates pressure in millimeters of mercury. The gauge indicator 130 shows a baseline pressure of 70 mm of mercury in the device with the subject at rest.

The schematic representation is of an ultrasound image taken using the apparatus simultaneously with the above recording of pressure, showing the skin 112, subcutaneous tissue 113, abdominis obliquus externus 114, abdominis obliquus internus 115 and transversus abdominis 116 at rest.

The EMG display shows an absence of muscular activity at rest and establishes a baseline of activity.

Figure 16:
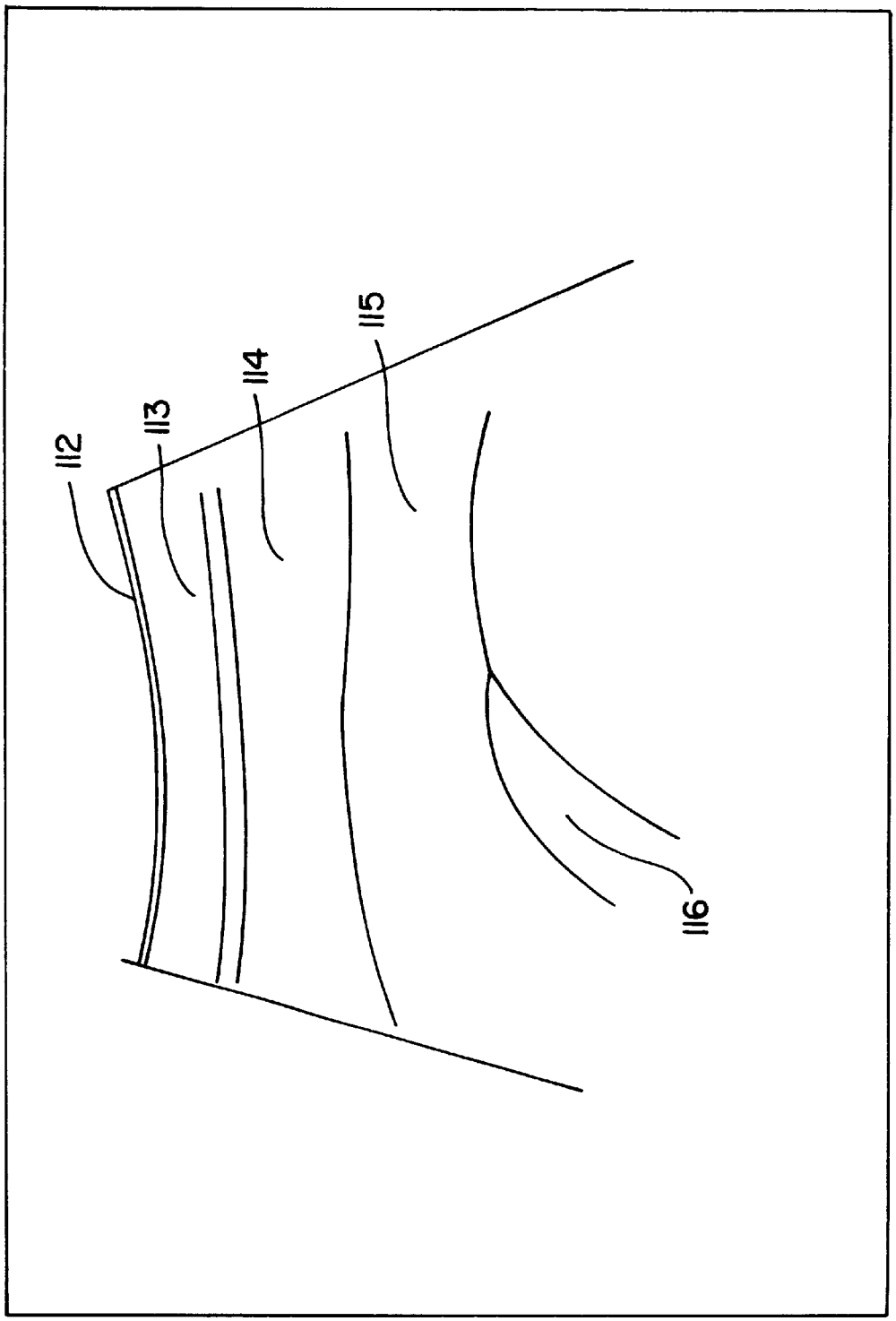
FIGS. 16 & 17 show simultaneous readings of the muscle function assessment apparatus attached to a subject performing a correct abdominal drawing in action.
Figure 17:
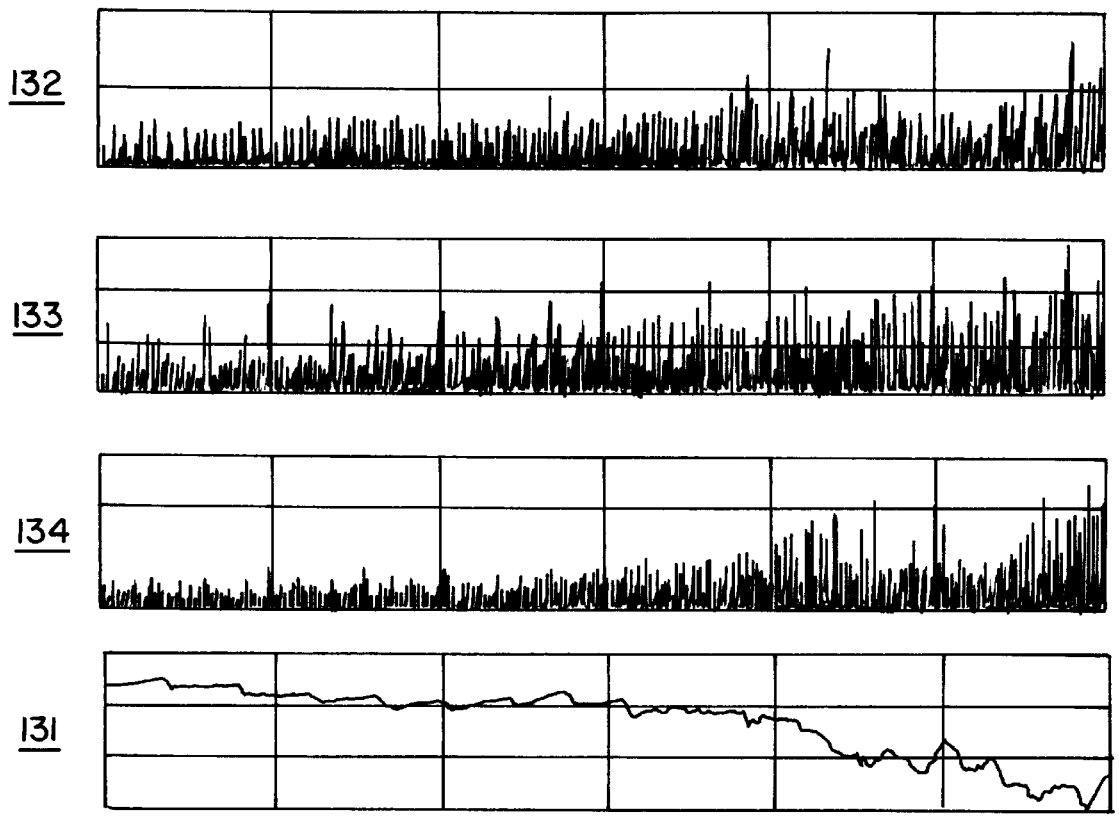

FIGS. 16 and 17 show similar recordings to FIG. 15 during correct performance of the abdominal drawing in action except that the pressure biofeedback monitor is in an alternative form and produces a trace reading 131.

The schematic representation is of an ultrasound image generated simultaneously with the recording of pressure. The transversus abdominis 116 contracts and also increases its width on contraction. There is little change in the superficial muscles 114, 115. During the correct performance of the abdominal drawing in action, the pressure as indicated in the pressure biofeedback aspect of the apparatus reduces by 6 to 10 millimeters of mercury, as shown in FIG. 17. The EMG tracing shows the superficial muscles abdominis obliquus externus 132, abdominis obliquus internus 133 and rectus abdominis 134, particularly when compared to the trace of FIG. 19, during performance of the drawing in action after the line 124. The superficial muscles show only a slight increase in activity during proper performance of the activity.

Figure 18:
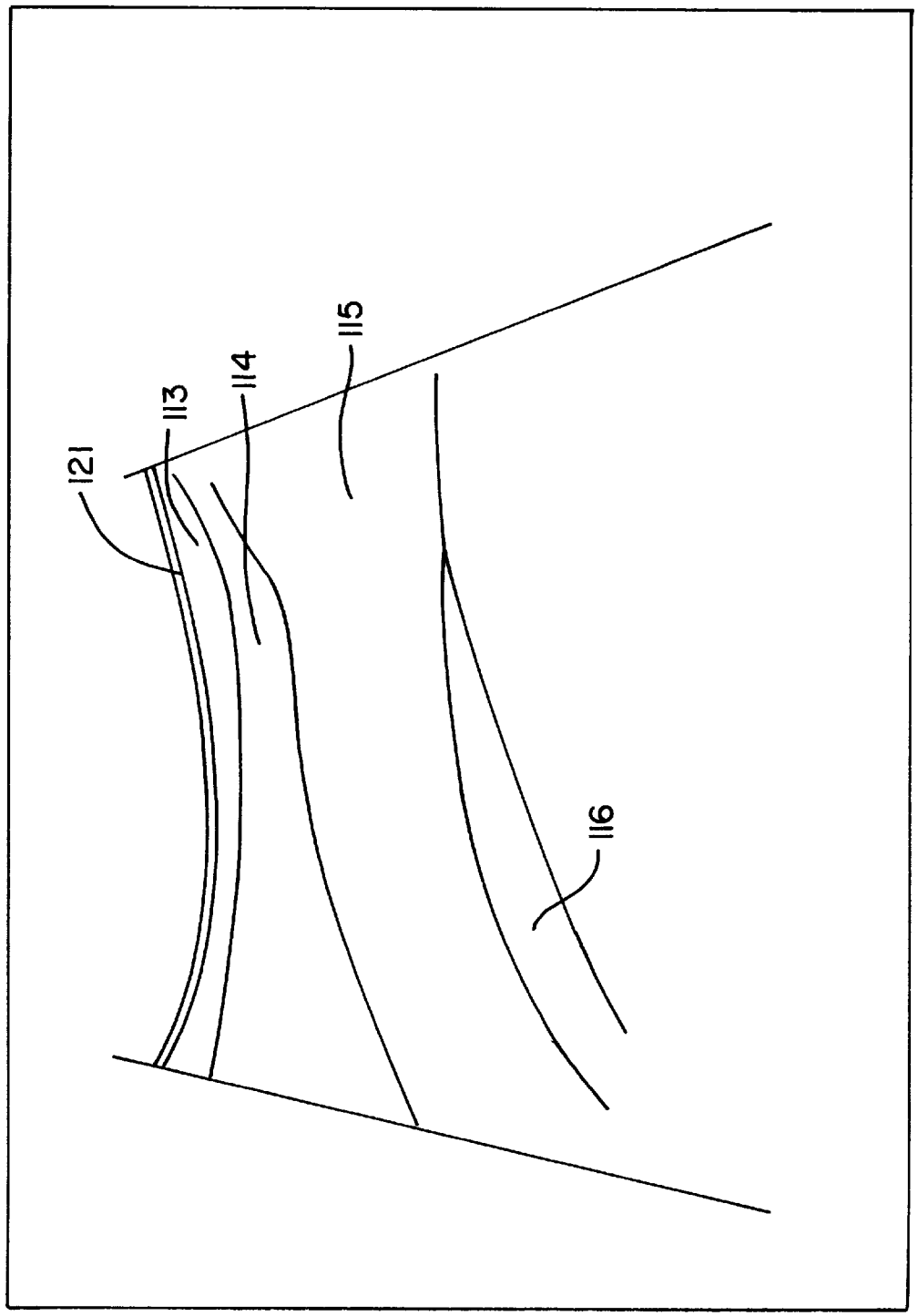
FIGS. 18 & 19 show simultaneous readings of the muscle function assessment apparatus attached to a subject performing an incorrect abdominal drawing in action.
Figure 19:
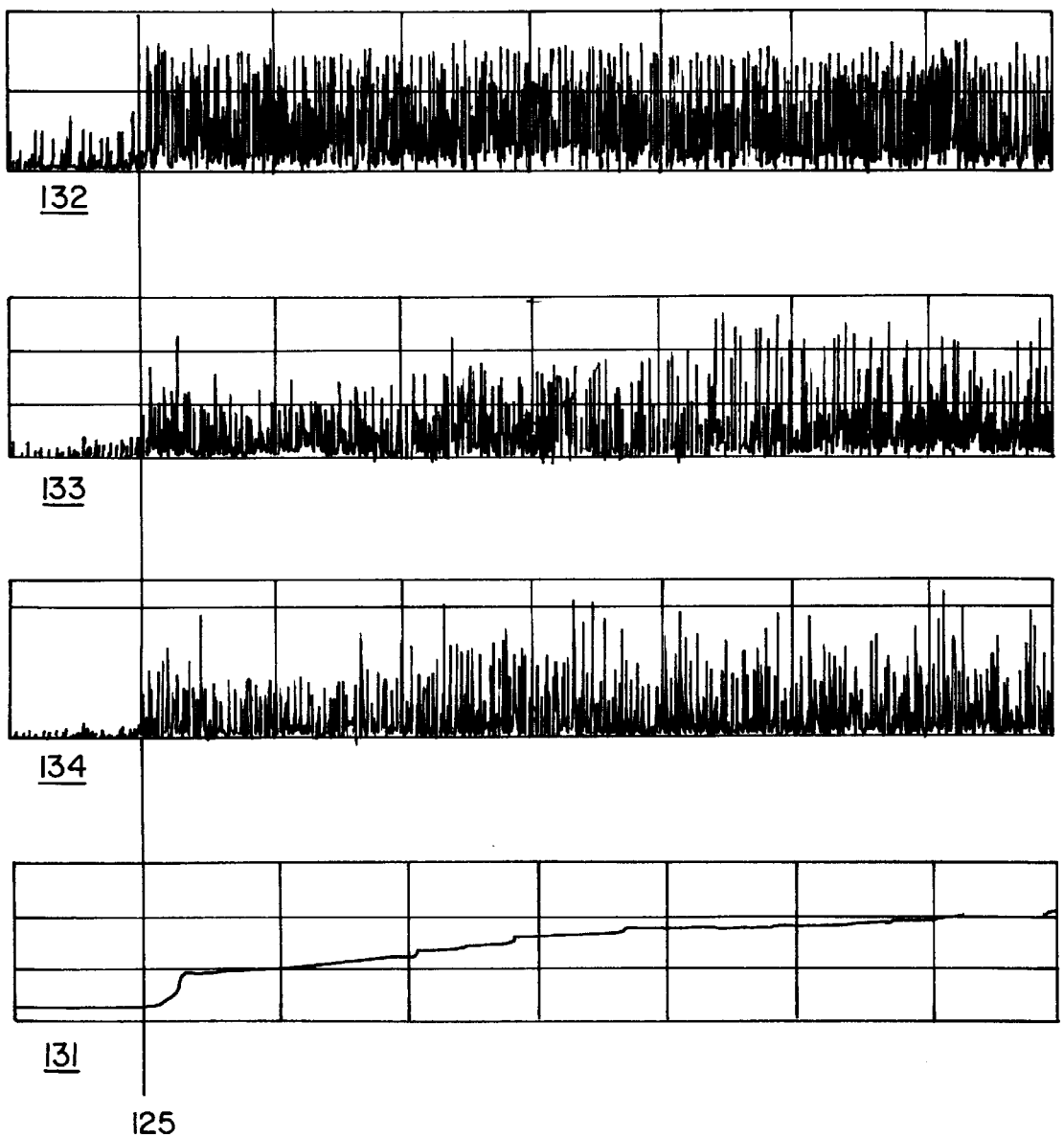

FIGS. 18 and 19 show recordings of the muscle function assessment apparatus during incorrect abdominal drawing in.

The representation of the ultrasound image in FIG. 18 shows contraction of all muscles of the abdominal wall simultaneously rather than the preferred substantially isolated contraction of the transversus abdominis. In fact, the abdominis obliquus externus 114, abdominis obliquus internus 115 and transversus abdominis have contracted together and each has increased its depth, although the change in transversus abdominis 116 is not as pronounced or as prolonged as during correct performance of the action. In FIG. 19, the pressure biofeedback monitor 131 registers a slight increase in pressure rather than a decrease. A drop of less than 2 mm of mercury, no change in pressure or an increase in pressure is a poor result and indicates that the subject is unable to contract the transversus abdominis into its shortened range, independently of the other abdominal muscles. The EMG tracing shows superficial muscles during performance of the above abdominal drawing in action after line 125. As can be seen, the muscle activity is marked after onset of the activity indicating recruitment of the superficial musculature rather than the desired use of the transversus abdominis. This is particularly obvious in the abdominis obliquus externus 132 and abdominis obliquus internus 133. The EMG traces may be further analysed by calculation of an RMS value for each one.

Figure 20:
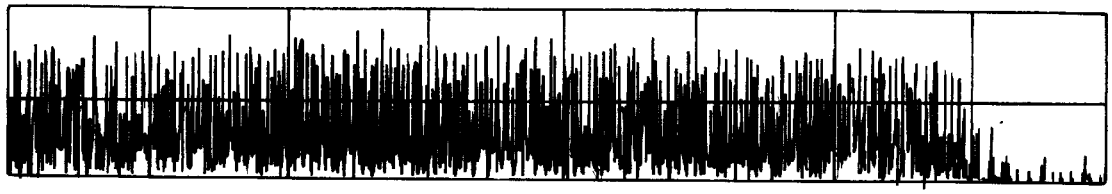
FIG. 20 shows EMG tracings for superficial muscles during a substantial level of activity.
Figure 20:
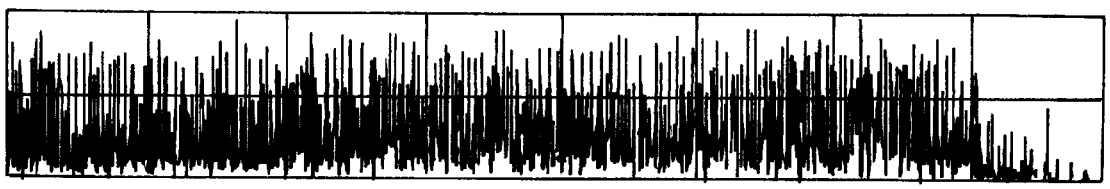
Figure 20:
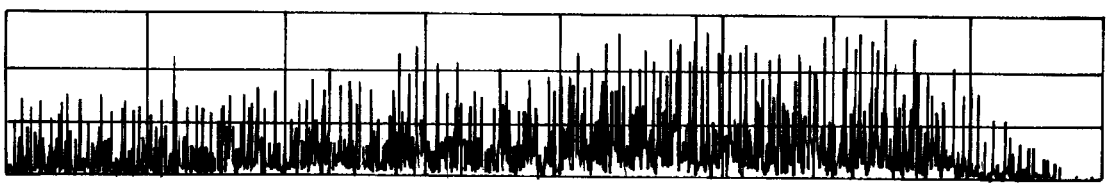

FIG. 20 shows an EMG tracing for the abdominis obliquus externus 135, abdominis obliquus internus 136 and rectus abdominis 137 during forced expiration on a vitalograph. This result gives a substantial level of EMG activity against which recordings during testing may be compared.

These methods with suitable modifications to suit the location of the muscle may be used to assess the function of any deep stabilizing muscles of the neck, spinal joints or the proximal peripheral joints including the knee, hip and shoulder.

The advantages of the claimed invention include the ability to provide a reliable indication of deep muscle function. This may be used to identify people at risk of joint instability. An obvious application is to screen the suitability of candidates for employment activities involving lifting. The techniques may also identify exercise regimes for prevention and rehabilitation which exercise the important muscles for joint stability and thereby avoid effort expended on exercises which are ineffective in recruiting the targeted muscles. Previously the only known techniques offering remotely similar information on deep musculature involved find needle insertion into the muscles. This technique is impractical for wide usage and is effectively restricted to experimental or specialized applications.

Clearly, the disclosed method of assessment and apparatus are also ideally suited to monitor the effects and improvements of any therapeutic exercise regime.

The preferred embodiments described herein are intended to illustrate the principles of the invention but not to limit the scope. Other embodiments and variations to the preferred embodiments maybe evident to those skilled in the art and may be made without departing from the spirit and scope of the invention.

We claim:

1. A method of assessment of the function of at least one deep muscle of a subject including the steps of:
    establishing a baseline level of activity of at least one superficial muscle;
    monitoring the activity of said at least one superficial muscle while the subject performs at least one prescribed activity; and
    analyzing the activity of said at least one superficial muscle during the prescribed activity and the baseline level of activity of said at least one superficial muscle to produce an indication of the function of said at least one deep muscle.

2. The method of claim 1 further including the step of displaying the indication of function on display means.

3. The method of claim 1, wherein monitoring of the activity of said at least one superficial muscle is performed using EMG means.

4. The method of claim 1, wherein the prescribed activity is an exercise known to require substantial contraction of at least one deep muscle under assessment when the prescribed activity is performed correctly.

5. The method as claimed in claim 1, further including the step of monitoring the activity of said at least one deep muscle, simultaneously while monitoring the activity of said at least one superficial muscle and analyzing the activity of said at least one deep muscle to provide an indication of the function of said at least one deep muscle.

6. The method of claim 5, wherein the monitoring of said at least one deep muscle is performed using pressure monitoring means.

7. The method of claim 5, wherein monitoring of the activity of said at least one deep muscle includes using visualizing means.

8. The method of claim 5, wherein the monitoring of said at least one deep muscle is performed by using both visualizing means and pressure monitoring means.

9. The method of claim 5, further including the steps of:
varying the position of the subject;
varying the activities performed by the subject;
monitoring superficial muscle activity during said activities;
monitoring deep muscle activity during said activities; and
identifying positions or activities in which deep muscle use is significant.

10. The method of claim 9, further including the step of selecting exercises for deep muscle training based on the identification of positions or activities in which deep muscle use is significant.

11. A method of assessment of the function of at least one deep muscle of a subject including the steps of:
establishing a baseline level of activity of at least one superficial muscle;
monitoring the activity of said at least one superficial muscle while the subject performs at least one prescribed activity;
analyzing the activity of said at least one superficial muscle during the prescribed activity and the baseline level of activity of said at least one superficial muscle to produce an indication of the function of said of at least one deep muscle;
monitoring the activity of said at least one deep muscle, simultaneously when monitoring the activity of said at least one superficial muscle and analyzing the activity of said at least one deep muscle to provide an indication of the function of said at least one deep muscle; and
further including the step of establishing a substantial level of activity of said at least one superficial muscle and analyzing the substantial level of activity to give an indication of function of said at least one deep muscle.

12. The method of claim 11, wherein the step of establishing the substantial level of activity of said at least one superficial muscle includes monitoring said at least one superficial muscle while the subject performs an exercise known to require substantial input from said at least one superficial muscle.

13. The method of claim 11, wherein the monitoring of said at least one superficial muscle includes using EMG means.

14. The method of claim 11, wherein analysis is performed using a processor programmed to analyze data from one or more monitoring means.

15. The method of claim 11, further including the steps of:
varying the position of the subject;
varying the activities performed by the subject;
monitoring superficial muscle activity during said activities;
monitoring deep muscle activity during said activities; and
identifying positions or activities in which deep muscle use is significant.

16. The method of claim 15, further including the step of selecting exercises for deep muscle training based on the identification of positions or activities in which deep muscle use is significant.

17. An apparatus for assessing the function of at least one deep muscle comprising:
means for establishing signals indicative of a baseline level of activity of at least one superficial muscle;
monitoring means to monitor activity of said at least one superficial muscle and produce signals characteristic of muscle activity;
display means to display the signals indicative of a baseline level of activity and the signals characteristic of muscle activity of said at least one superficial muscle; and
analysis means to analyze the signals indicative of a baseline level of activity in relation to the signals characteristic of muscle activity of said at least one superficial muscle to produce an indicator of the function of said at least one deep muscle.

18. The apparatus of claim 17, wherein the means for establishing signals indicative of a baseline level of activity and the means for monitoring superficial muscle activity are EMG means.

19. The apparatus of claim 17, wherein the means for establishing signals indicative of a baseline level of activity and the means for monitoring superficial muscle activity are ultrasound imaging means.

20. The apparatus of claim 17, wherein the analysis means is at least one processing means programmed to perform analysis of data in relation to the baseline level of activity and said activity of the at least one superficial muscle.

21. The apparatus of claim 20, wherein the processing means is in signal connection with the means for establishing signals indicative of a baseline level of activity and the means for monitoring superficial muscle activity.

22. The apparatus of either of claim 20 or 21, wherein the processing means is programmed to analyze data according to the algorithm:

$$a(t) \propto \frac{1}{m-b}$$

where:
a is the function of the deep muscle,
t is the time of contraction
m is the activity of the superficial muscle; and
b is the baseline activity of the superficial muscle.

23. The apparatus of claim 17, further comprising pressure monitoring means for monitoring changes in force exerted by muscles.

24. The apparatus of claim 23, wherein the analysis means further comprises processing means programmed to perform an analysis of data received from the pressure monitoring means to give an indication of muscle of the at least one deep muscle.

25. The apparatus of claim 24, wherein the pressure monitoring means is in signal connection with the processing means.

26. The apparatus of either of claims 24 or 25, wherein the analysis means further comprises processing means programmed to analyze the data according to the algorithm:

$$a \, \Delta P$$

where $\Delta P$ is the difference between p1 and p;

wherein p1 is a level of the monitored pressure recorded when the subject is at rest;

p is the pressure recorded during the performance of an activity;

p2 is a set limit of the monitored pressure; and p is between p1 and p2.

27. The apparatus of claim 17, further comprising visualizing means to view said at least one deep muscle.

28. The apparatus of claim 27, wherein the visualizing means is ultrasound imaging means.

29. The apparatus of claim 27, wherein the analysis means further comprises processing means programmed to perform an analysis of data from the visualizing means to give an indication of function of the at least one deep muscle.

30. The apparatus of claim 29, wherein the visualizing means is in signal connection with the processing means.

31. The apparatus of claim 17, further comprising means for establishing a substantial level of activity of said at least one superficial muscle.

32. The apparatus of claim 31, wherein the processing means is programmed to analyze the data according to the algorithm:

$$a(t) \propto \frac{s-b}{m-b}$$

where:

a is the function of the deep muscle t is the time of contraction m is the activity of the superficial muscle b is the baseline activity of the superficial muscle; and s is the substantial level of activity of a superficial muscle as detected by the superficial muscle monitoring means.

33. The apparatus of claim 31, wherein the means for establishing a substantial level of activity of said at least one superficial muscle is a vitalograph.

34. An apparatus for assessing the function of at least one deep muscle comprising:

means for establishing signals indicative of a baseline level of activity of at least one superficial muscle;

monitoring means to monitor activity of said at least one superficial muscle and produce signals characteristic of muscle activity;

display means to display the signals indicative of a baseline level of activity and the signals characteristic of muscle activity of said at least one superficial muscle;

pressure monitoring means for monitoring changes in force exerted by muscles;

visualizing means to view said at least one deep muscle; and analysis means to analyze the signals indicative of a baseline level of activity in relation to the signals characteristic of muscle activity of said at least one superficial muscle, the changes in force exerted by muscles and changes visualized in said at least one deep muscle, to produce an indicator of the function of said at least one deep muscle.

35. The apparatus of claim 34, further comprising means for establishing a substantial level of activity of said at least one superficial muscle.

* * * * *